US005458468A

United States Patent [19]
Ye et al.

[11] Patent Number: 5,458,468
[45] Date of Patent: Oct. 17, 1995

[54] DIAPHRAGM PUMP

[75] Inventors: Chun-Xia Ye, Shanghai, China; Mitsuo Umezu, Osaka, Japan; Allen H. Nugent, Victoria, Canada

[73] Assignee: Victor Peter Chang, New South Wales, Australia

[21] Appl. No.: 218,153

[22] Filed: Mar. 25, 1994

Related U.S. Application Data

[63] Continuation of Ser. No. 79,361, Jun. 18, 1993, abandoned, which is a continuation of Ser. No. 863,355, Mar. 31, 1992, abandoned, which is a continuation of Ser. No. 555,382, filed as PCT/AU89/00554, Dec. 22, 1989, abandoned.

[30] Foreign Application Priority Data

Dec. 29, 1988 [AU] Australia .................... PJ2128

[51] Int. Cl.$^6$ ................................ F04B 43/06
[52] U.S. Cl. ........................... 417/395; 623/3
[58] Field of Search ...................... 417/394, 395; 604/141, 153; 623/3; 415/900; 128/DIG. 12

[56] References Cited

U.S. PATENT DOCUMENTS

| | | | |
|---|---|---|---|
| 3,769,960 | 11/1978 | Robinson | 128/10 |
| 3,974,825 | 8/1976 | Normann | 623/3 |
| 4,222,127 | 9/1980 | Donachy | 623/3 |
| 4,381,567 | 5/1983 | Robinson | 417/394 |
| 4,578,077 | 3/1986 | Joh | 623/3 |
| 4,976,730 | 12/1990 | Kwan-Gett | 623/3 |
| 5,006,104 | 4/1991 | Smith | 417/395 |
| 5,011,380 | 4/1991 | Kovacs | 417/413 |

FOREIGN PATENT DOCUMENTS

| | | |
|---|---|---|
| 0291476A2 | 11/1988 | European Pat. Off. . |
| 851143 | 1/1987 | France . |
| 2542392 | 3/1977 | Germany . |
| 3130646A1 | 2/1983 | Germany . |
| 2151244A | 7/1985 | United Kingdom . |
| WO87/00060 | 1/1987 | WIPO . |

OTHER PUBLICATIONS

Abstract SU1405–841–A, May 22, 1986.
Abstract SU1175–493–A, Jul. 13, 1983.

*Primary Examiner*—Richard A. Bertsch
*Assistant Examiner*—Peter G. Korytnyk
*Attorney, Agent, or Firm*—Limbach & Limbach

[57] ABSTRACT

A pump (10) has a housing (11), a base (12) and a flexible diaphragm (13) between the housing and the base. The diaphragm (13) and the base (12) define a driving chamber and the diaphragm (13) and the housing (11) define a pump chamber. The driving chamber is coupled to a pump driver adapted to direct fluid to and from the driving chamber to drive the diaphragm. The pump chamber is of generally conical form with its outlet (21) being located at the apex of the conical pump chamber and the inlet (22) being disposed at an angle inclined to the plane of the base of the conical pump chamber and being generally tangential to the outer portion of the base of pump chamber such that flow through the pump chamber is in the form of a continuous spiral vortex.

14 Claims, 9 Drawing Sheets

PUMP PERFORMANCE CURVES of the SPIRAL VORTEX PUMP.

FREE PLASMA HEMOGLOBIN IN TWO DIFFERENT TYPES of BLOOD PUMP. (PUMP FLOW RATE: 3 L/min at 60 BPM)

DIAPHRAGM PUMP

This is a continuation of application Ser. No. 08/079,361 filed on Jun. 18, 1993(which has been abandoned), which is a continuation of application Ser. No. 07/863,355 filed Mar. 31, 1992 (which has been abandoned), which is a continuation of application Ser. No. 07/555,382 filed Aug. 2, 1990 ( which has been abandoned).

FIELD OF INVENTION

This invention relates to pumps having a diaphragm which separates a diaphragm-driving fluid from a fluid to be pumped. A drive, which is usually external of the pump, controls the flow of driving fluid so as to generate the pumping action of the diaphragm.

Such pumps may be used in a wide variety of fluid circuits including ventricular assist devices (i.e. non-implantable artificial hearts), implantable or total artificial hearts, heart pumps and other circulatory support devices as well as for arterial support and renal perfusion.

BACKGROUND ART

The most important clinical problems with heart pumps and other circulatory support devices including those for end-stage heart disease are thrombosis and thromboembolysm. While these factors can be controlled by anti-coagulant therapy, long term application of anti-coagulant drugs generally induces uncontrolled bleeding. Thrombogenicity primarily arises from mechanical or chemical interaction with foreign materials, high mechanical stresses arising from unnatural flow patterns and transient pressures and/or the tendency of blood to clot in regions of stationary flow.

Clinical experience with total artificial hearts is somewhat limited. Thus far, there have only been a few permanent and over one hundred bridge-use implantations of the total artificial heart and these have occurred mainly in the United States of America and France.

Ventricular assist devices have been used many times for temporary support of diseased hearts in the United States of America, Japan and European countries. The greatest hindrances to the clinical and commercial success of these devices have been thrombogenicity, mechanical failure of valves, complicated and labour-intensive fabrication process and high costs.

The thrombogenicity of circulatory support devices arises from several structural and functional factors. Blood elements are damaged by contact with foreign materials through mechanical and electro-chemical interactions. The valve-mounting areas and the diaphragm-housing junction of the pump chamber are the main sites for thrombus formation by these mechanisms. Hemolysis is induced by excessively-high sheer stresses which occur when adjacent streams of fluid have sufficiently different velocities and by high transient pressures produced by valve closure—the "water hammer" effect. Both these conditions occur predominantly near the inflow/outflow conduits and valves of the blood pump. Regions of flow stasis may occur within the pump chamber itself. Overcoming these problems is one of the greatest challenges in the field of chronic circulatory support.

Another factor which bears upon the design of a pump for circulatory support devices is the importance of reducing (or preferably eliminating) the need for anti-coagulant therapy for long term circulatory support.

There are physiological and other advantages arising from continuous pulsatile blood flow rather than non-pulsatile flow through a circulatory support device. Continuous blood flow helps eliminate stasis and/or stagnation of the bleed flow but may induce high shear stress. Pulsatile flow produces an aortic waveform which is similar to the natural waveform.

Prior art pumps which provide pulsatile flow include centrifugal pumps which do not have valves and diaphragm pumps which do have valves.

Centrifugal pumps use mechanical stirring as the driving force. As valves are not used, the resting state of the pump is achieved by driving the blood to create a flow rate which equalises the back flow caused by the afterload. Centrifugal pumps can be adapted to produce either steady flew or pulsatile sinusoidal flow.

In the past, it was asserted that homolysis resulting from stirring (as in the case of centrifugal pumps) was balanced by homolysis caused by valves through the water hammer effect and cavitation (as in the case of diaphragm pumps). However, recently developed valves such as the St. Vincent's mechanical heart valve which dramatically reduces the water hammer effect have enabled improvements to be made with diaphragm pumps.

The present invention is concerned with diaphragm pumps driven by pulsatile drivers and it is an object of the invention to provide such a pump which will provide improved blood flow characteristics, lower hemolysis and lower thrombogenicity.

DISCLOSURE OF THE INVENTION

According to one aspect of the invention there is provided a pump comprising a housing, a base, a flexible diaphragm between the housing and the base, with the diaphragm and the base defining a driving chamber and the diaphragm and the housing defining a pump chamber, an inlet to the pump chamber, an outlet from the pump chamber, a port in the driving chamber for coupling the driving chamber to a pump driver adapted to direct fluid to and from the driving chamber to drive the diaphragm, the pump chamber being of generally conical form with the outlet being located at the apex of the conical pump chamber and the inlet being disposed at an angle inclined to the plane of the base of the conical pump chamber and being generally tangential to the outer portion of the base of pump chamber such that flow through the pump chamber is in the form of a continuous spiral vortex.

In the preferred form of the invention, the pump is used for pumping blood and the blood enters the pump chamber tangentially to the existing blood flow to continue in a circular path around the periphery of the pump chamber causing least disruption to existing flaw within the pump chamber. The circular motion results in an effective washout of the diaphragm-pump chamber junction which traditionally has been an area of stagnation. Once within the pump chamber, the round axial cross-section of the pump chamber further evolves the circular movement of the blood. The inflowing blood fills the space created by the descending diaphragm. When the diaphragm ascends, the circulating blood is constrained by continuity and conservation of angular momentum and, as a result, farms a converging helix. The conical profile of the pump chamber results in the angular velocity increasing axially from the base plane. The apically located outlet offers a path of minimum resistance to the exit of the blood from the pump chamber.

The shape and movement of the diaphragm assists in advancing the spiral flaw towards the apex of the conical pump chamber, washes out all areas of the pump chamber and diaphragm and may reduce the amount of regurgitation through the inlet valve during systole. The resultant flow pattern eliminates flow separation and stagnation in the pump and between the conduits (as occurs in conventional pumps in which the conduits are co-planar and usually para-axial).

BRIEF DESCRIPTION OF THE DRAWINGS

In order that the invention may be more readily understood and put into practical effect, reference will now be made to the accompanying drawings in which.

DETAILED DESCRIPTION OF THE PREFERRED EMBODIMENTS

Figure 1:
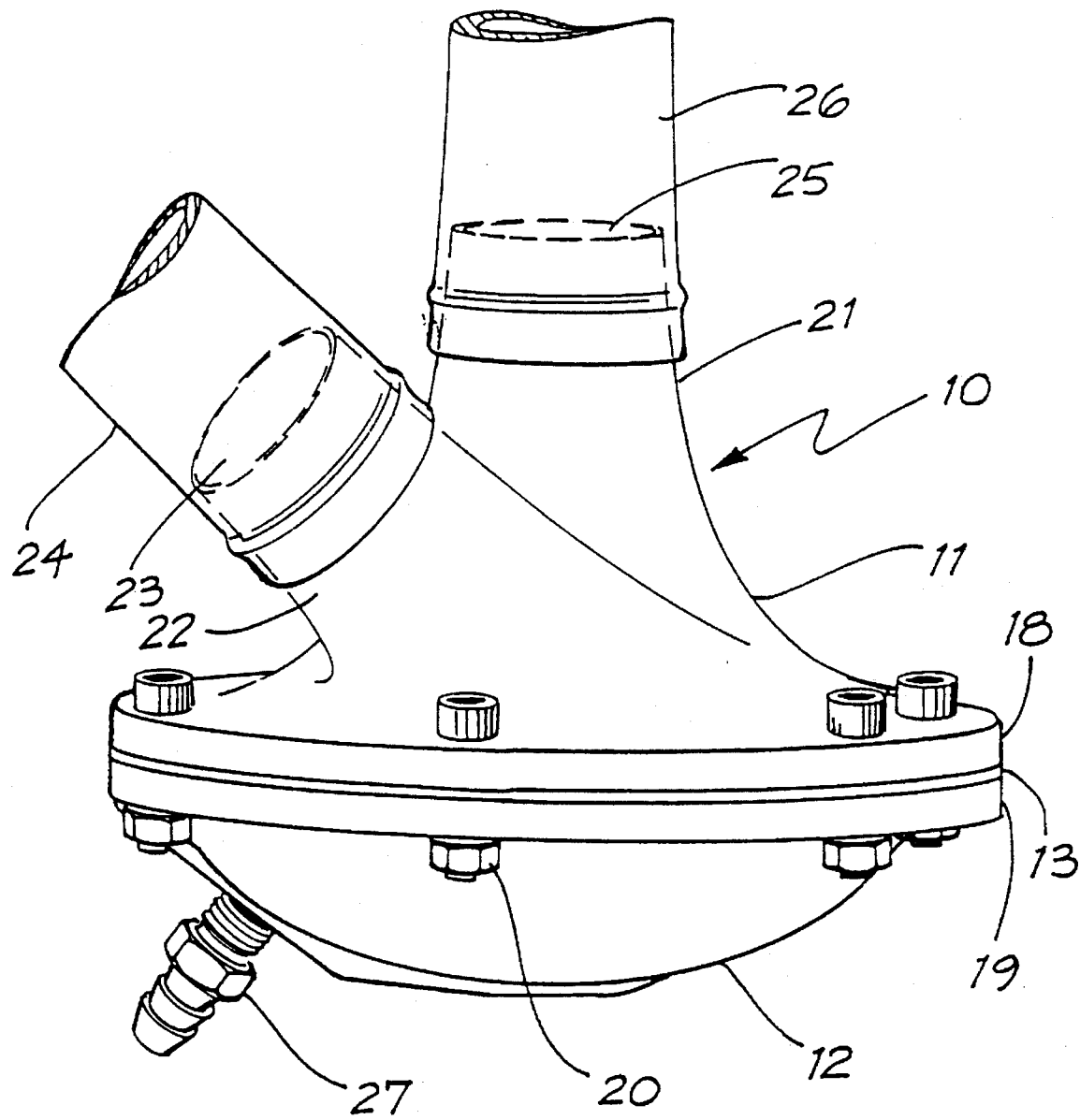
FIG. 1 is a perspective view of a pump for a circulatory support device according to one embodiment of the invention.
Figure 2:
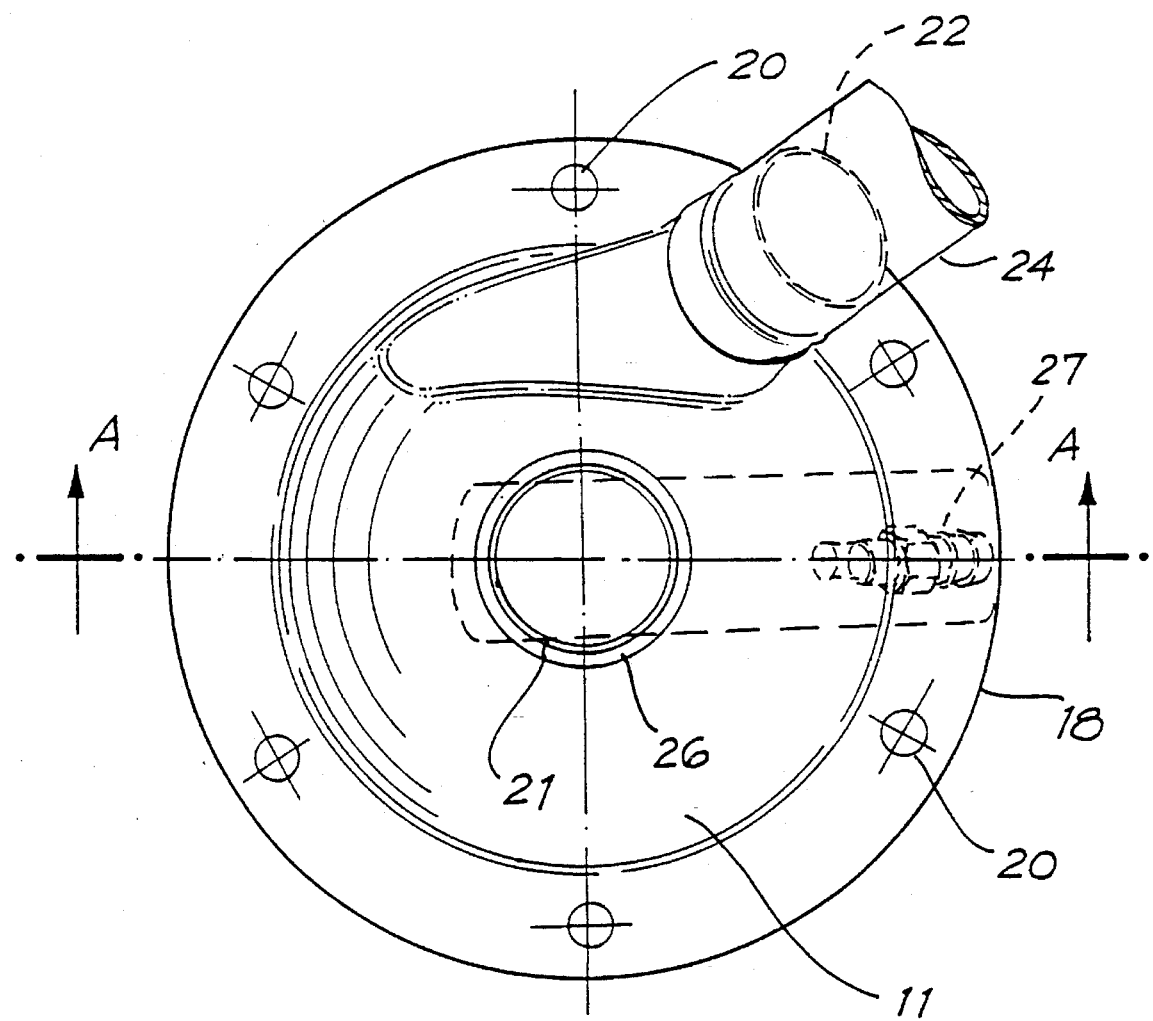
FIG. 2 is a plan view of the pump shown in FIG. 1.
Figure 3:
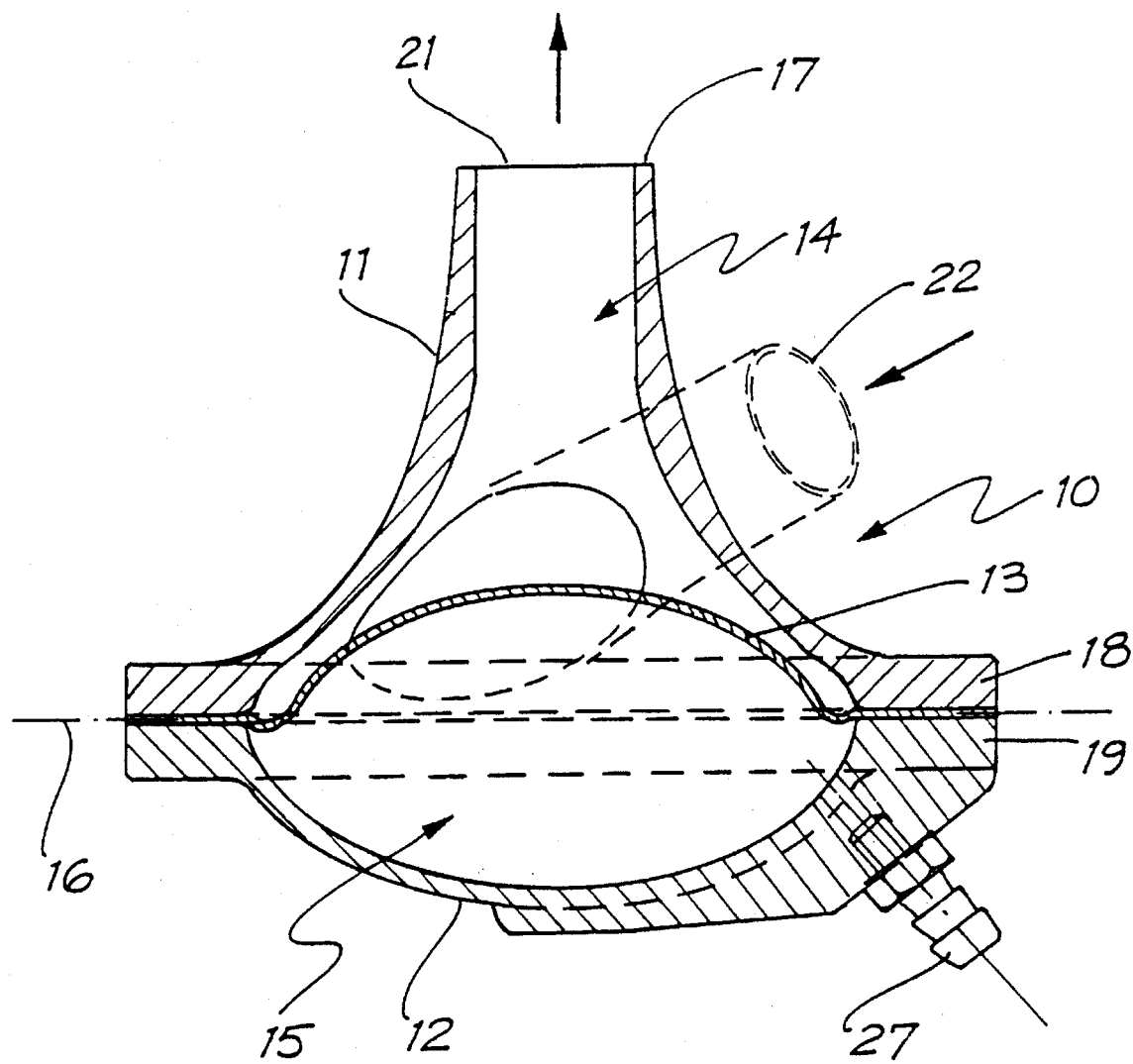
FIG. 3 is a view taken along lines A—A of FIG. 2.

The pump 10 shown in FIGS. 1 to 3 includes a pump housing 11, a base 12 and a driving diaphragm 13 therebetween. The pump housing 11 and the diaphragm 13 define a pump chamber 14 and the base 12 and the diaphragm 13 define a driving chamber 15.

The pump chamber 14 is of generally conical form with the base plane 16 of the cone adjacent to the base 12 and the apex 17 remote therefrom. At the base of the pump housing 11 there is an annular mounting flange 18 and at the top of the base 12 there is a co-operating annular mounting flange 19. The pump housing 11 and the base 12 are, in this instance, coupled together by means of bolts and nuts 20 which pass through the flanges 18 and 19. The flanges 18 and 19 may be coupled together by a circumferential clamping ring. The diaphragm 13 is clamped between and chemically bonded to the flanges 18 and 19 as can be seen in FIGS. 1 and 3.

At the apex 17 of the conical pump chamber 14 there is an outlet 21 which is perpendicularly disposed to the base plane 16. Adjacent to the base of the pump housing 11 there is an inlet 22 which, in this instance, intersects the base plane 16 at an angle of 45° to the vertical and is tangential to the outer portion of the base 12. An inlet valve 23 located in tubular valve housing 24 and outlet valve 25 located in tubular valve housing 26 will be described below in relation to FIGS. 5 to 8. The valve housings 24 and 26 are held in place on the inlet 22 and the outlet 21 respectively by means of cable ties (not shown).

The base 12 has a port 27 for coupling the driving chamber 15 to an external pump driver adapted to direct fluid to and from the driving chamber 15 which drives the diaphragm 13 in a pumping fashion. In this instance, the port 27 is incorporated in the base 12 near the inlet area and its longitudinal axis intersects the base plane 16 at an angle of 45° to the vertical. The external driver will be described below in relation to FIG. 4.

In the preferred form of the invention, the pump housing 11 and the base 12 are made of transparent epoxy. Carbon fibres are embedded into the epoxy around the inlet 22, the outlet 21, the transfer port 27 and the flanges 18 and 19 to augment the mechanical strength of the epoxy. The diaphragm 13 is, in this instance, formed of a sandwich of a bio-compatible material/polyvinylchloride/bio-compatible material.

After assembly of the components, possible areas of discontinuity such as the junction of the diaphragm 13 and the pup housing 11 and the junction of the valve housings 24 and 26 with the pump housing 11 are coated selectively with polysegmented polyurethane (a bio-compatible material) to eliminate any discontinuity. All blood contacting surfaces (including the interior surface of the pump chamber 14, the diaphragm 13, the interior of the valve housings 24 and 26 and the interior of inlet 22 and outlet 21) are also coated with a bio-compatible material.

It will be appreciated that all connections within the blood circuit must be made with the minimum of discontinuity. Thus, the inlet 22 and outlet 21 must be as thin as possible at their respective junctions with the pump housing.

In this instance, the pump chamber 14 has an inner diameter of 75 mm at the base plane 16 and the height of the pump chamber from the base plane 16 to the beginning of the outlet 21 is 38 mm. As can be seen in FIG. 3, the diaphragm 13 is of semi-spherical shape and in this instance, the depth at its centre is 20 mm. The distance between the top of the diaphragm 13 at the end-systole position at the beginning of the outlet 21 is 15 mm. The shade of the base 12 and the diaphragm 13 are complementary.

Figure 4:
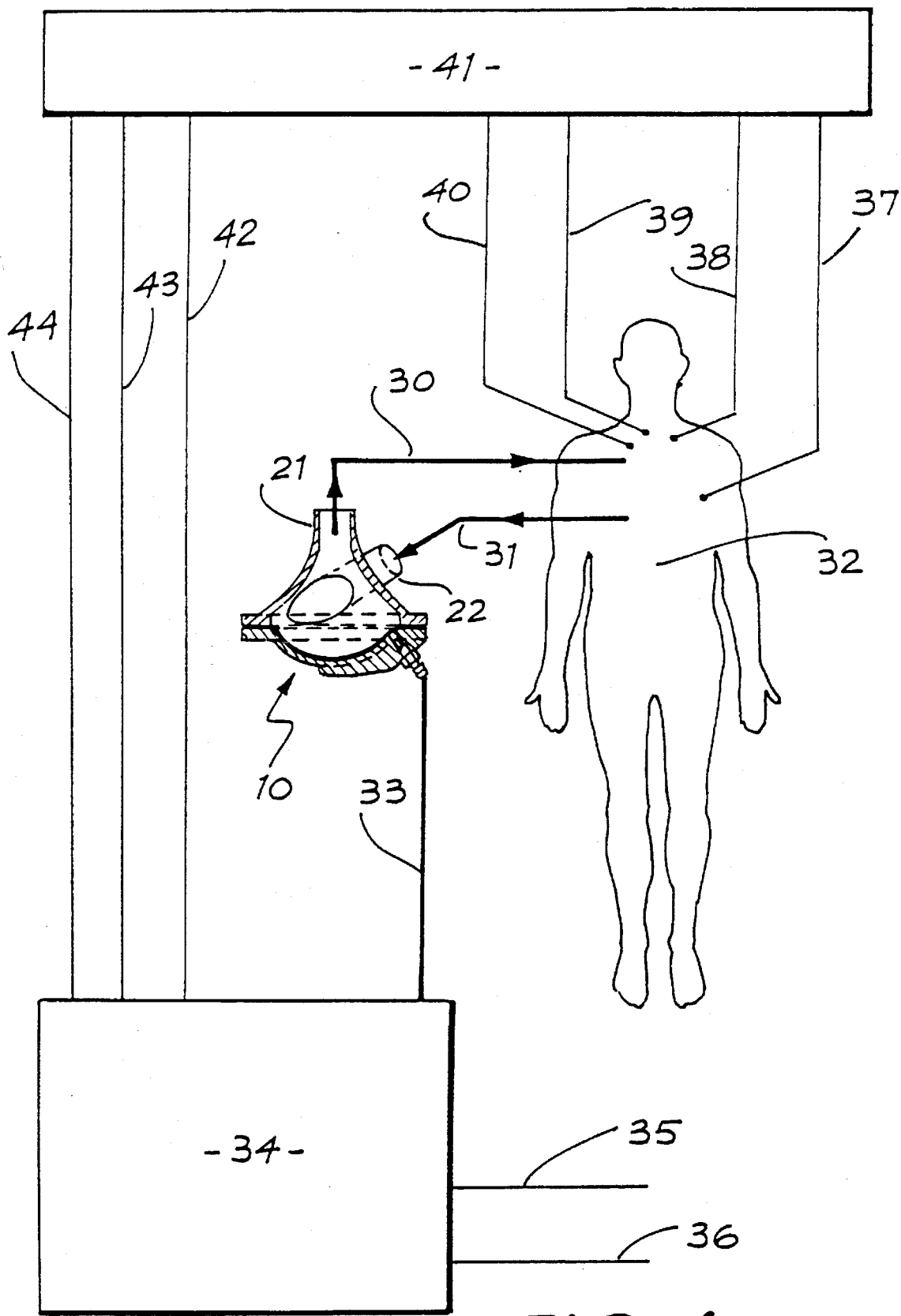
FIG. 4 is a schematic diagram of a circulatory support device incorporating the pump of FIGS. 1 to 3.

FIG. 4 is a schematic diagram of a circulatory support device incorporating the pump 10 of FIGS. 1 to 3. The outlet 21 of the pump 10 is connected through valve housing 26 to tubing 30 and leads, in the case of right ventrical support, into the pulmonary artery and the inlet 22 is coupled through valve housing 24 to tubing 31 connected by a withdrawal cannula placed in the right atrium of the patient 32.

The port 27 of the base 12 is connected by conduit 33 to controller 34 which in turn is coupled to compressed air supply line 35 and vacuum line 36. It is the function of the controller 34 to drive the diaphragm 13.

Line 37 provides an ECG signal from the patient 32 to a recorder 41. Line 38 provides a measure of atrial pressure from the patient 32 to the recorder 41, line 39 provides a measure of bypass flow and/or total flow from the patient to the recorder and line 40 provides a measure of aortic pressure to the recorder 41. Line 42 provides the ECG signal from the recorder 41 to the controller 34, line 43 provides the atrial pressure from the recorder 41 to the controller 34 and line 44 provides a measure of total flow from the recorder 41 to the controller 34.

As the function of the failing heart is reflected in the changes off left atrial pressure or total flow (cardiac output plus bypass flow) both the left atrial pressure and total flow can be automatically maintained within preset ranges simultaneously by changing the pumping duration in one cardiac cycle (the %-systole).

The inlet valve 23 shown in FIGS. 5 to 8 has a disc 45 located within a ring 46. The disc 45 has an annular flange 47 which locates the disc 48 between lower support strut 48 and upper support strut 49 integral with the ring 46.

Figure 5:
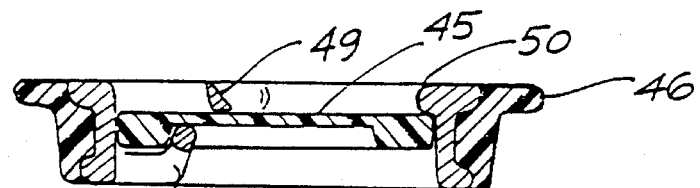
FIG. 5 is a perspective view of a valve for the pump shown in FIGS. 1 to 3 in its closed position.
Figure 6:
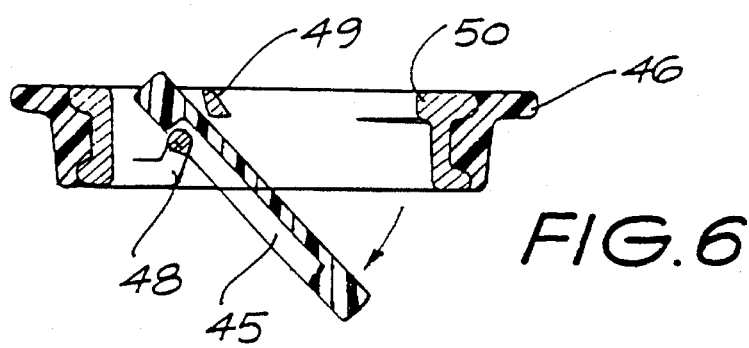
FIG. 6 is a view similar to FIG. 5 with the valve partially open.
Figure 7:
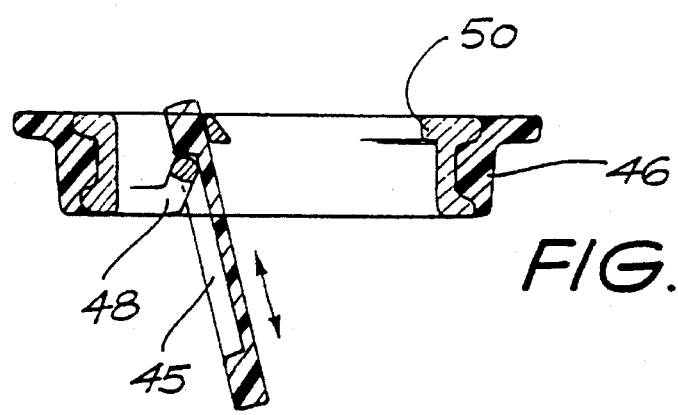
FIG. 7 is a view similar to FIG. 6 with the valve fully opened.
Figure 8:
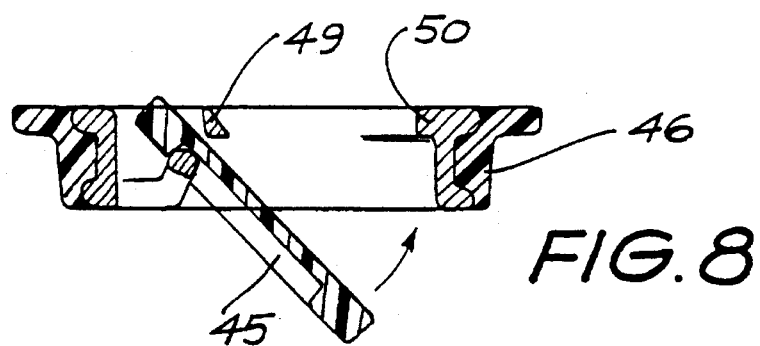
FIG. 8 is a view similar to FIG. 7 with the valve partly closed.

The valve is shown closed in FIG. 5 where the upper face of the disc 45 rests against an inwardly directed flange 50 of the ring 46. As the valve opens (see FIG. 6) the disc 45 both pivots and slides to its fully opened position as shown in FIG. 7. In the fully opened position, the flange 47 engages the lower support strut 48. When returning to the closed position (see FIG. 8), the disc 45 slides back into the ring 46 and finally pivots back into the closed position as shown in FIG. 5.

Although tissue valves have not traditionally been used in assist devices because of their bulky frames and other difficulties, it is possible that they may be used with the pump of the present invention. Plastic elastomeric valves may also prove to be usable.

Figure 9:
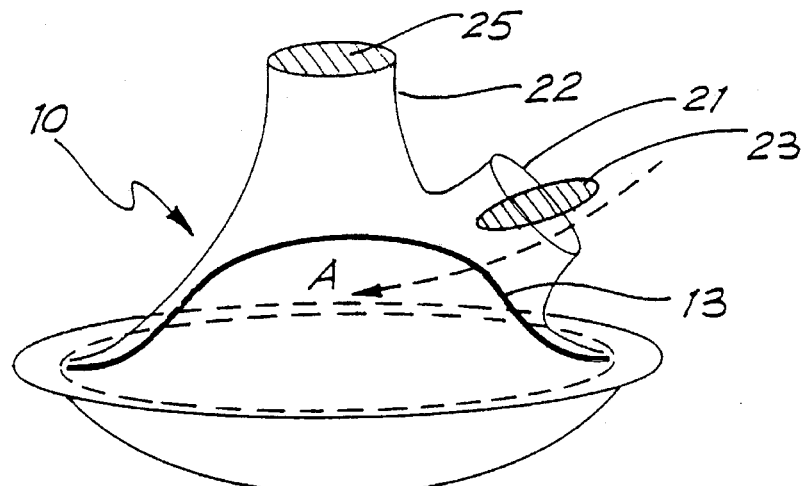
FIG. 9 is a schematic representation of the pump shown in FIGS. 1 to 3 at the start of diastole.

FIG. 9 represents the start of diastole in the cardiac cycle when the inlet valves 23 is open and the outlet valve 25 is closed and shows the configuration of the diaphragm 13 at the commencement of inlet flow of blood in the direction of arrow A.

Figure 10:
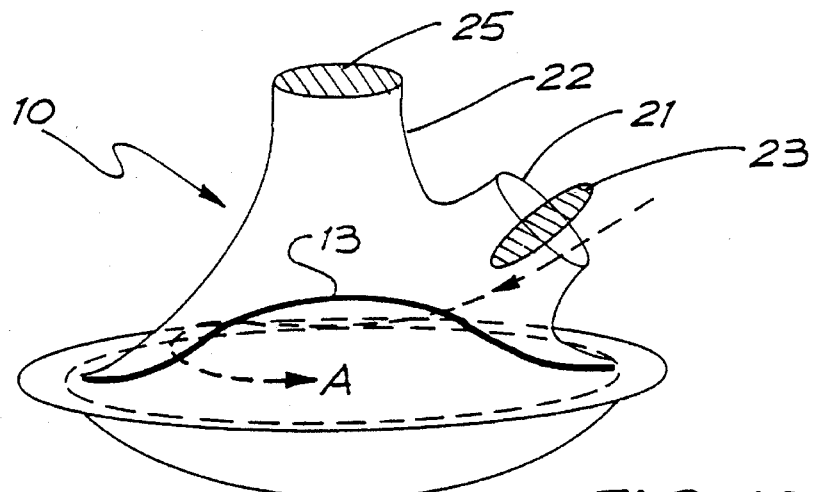
FIG. 10 is a schematic representation similar to FIG. 9 at the midpoint of diastole.

FIG. 10 represents middle diastole where the blood flow pattern is clearing the junction of the diaphragm 13 and the pump housing 11 as well as the surface of the diaphragm 13.

Figure 11:
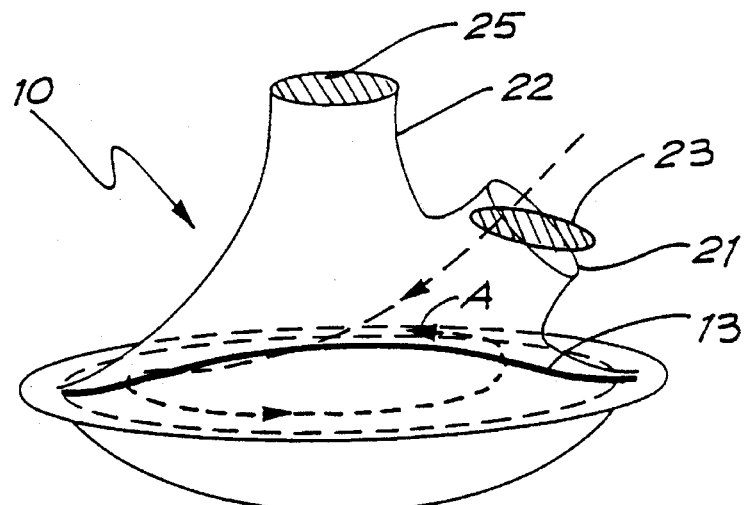
FIG. 11 is a schematic representation similar to FIG. 10 at late diastole.

FIG. 11 represents late diastole when the inlet valve 23 commences to close and shows the formation of the spiral motion of the blood as the diaphragm 13 moves lower in the driving chamber 15.

Figure 12:
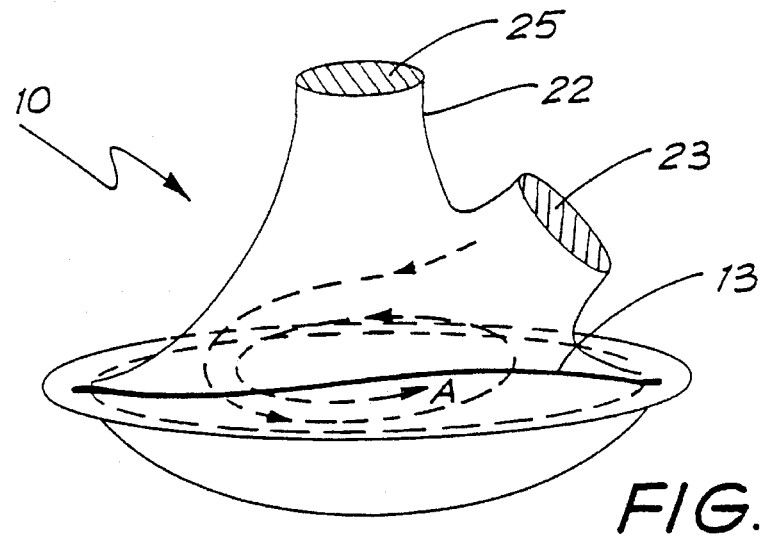
FIG. 12 is a schematic representation similar to FIG. 11 at full diastole.

At full diastole (shown in FIG. 12) the inlet 21 is closed and the spiral motion of the blood flow continues to develop as indicated by arrow A.

Figure 13:
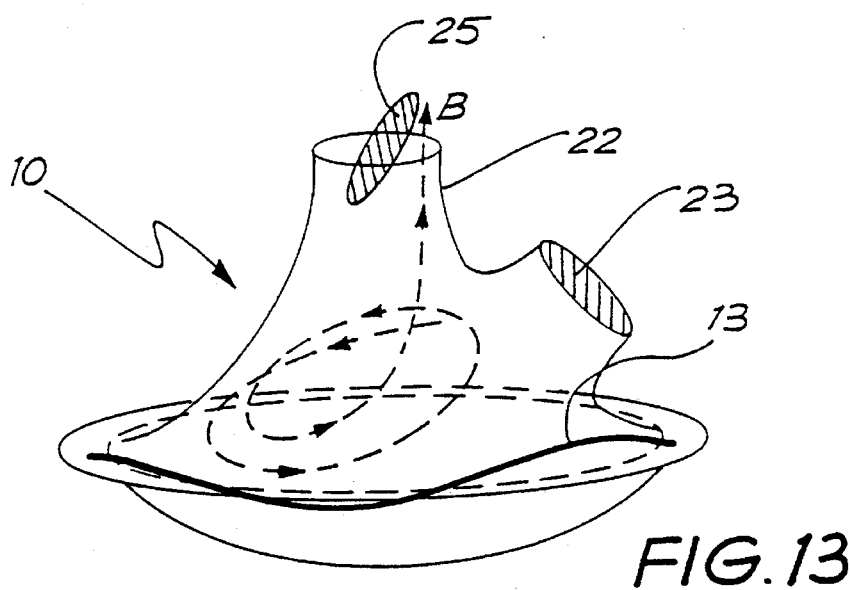
FIG. 13 is a schematic representation similar to FIG. 12 at the start of systole.

FIG. 13 represents the start of systole until the outlet 22 opened so that outflow begins. As described above, the outlet 22 is located at the apex of the conical pump chamber 14 so that during systole, the flow is directed in a convergent helical fashion through the outlet 22 as indicated by arrow B. Smaller volume of regurgitation through the inlet valve occurs due to the position of the diaphragm 13.

Figure 14:
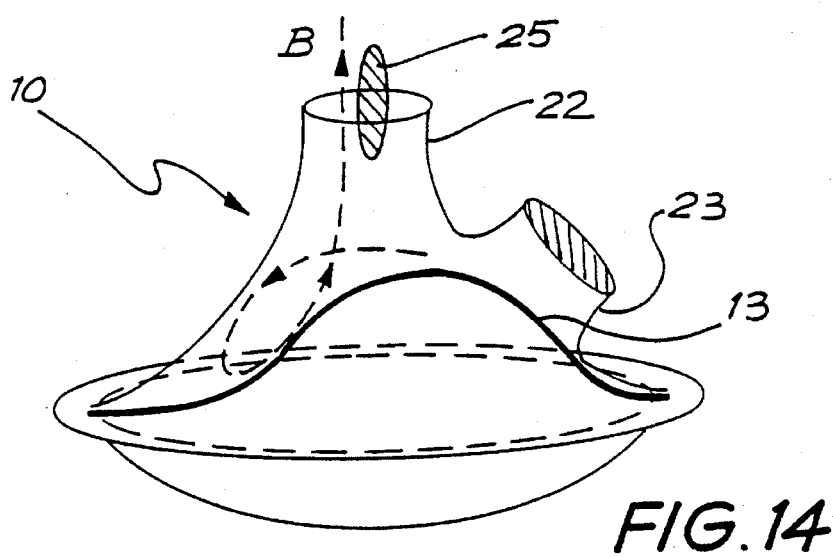
FIG. 14 is a schematic representation similar to FIG. 13 at late systole.

FIG. 14 represents late systole where blockage of the inlet 21 by the diaphragm 13 provides, in this instance, low regurgitation through the inlet valve 23 and where there is good washout in traditionally stagnant areas of the pump chamber 14. The end of systole is show in FIG. 9.

The flow pattern characteristics of the pump shown in FIG. 1 to 3 were compared with those of a conventional pneumatic pump. The conventional style pump chosen as a control had paraxial inlet and outlet ports. The flow patterns were visualized using water with ambolite particles as tracers in a mock circulatory system. It was shown that during diastole of the spiral-vortex pump of the invention, there was a circular inlet flow stream, that steadily involved the entire flow field in a coherent spiral vortex.

The 45° angled tangential entry of blood from the inlet port 21 and the continuous spiral flow pattern resulted in a good washout of the diaphragm-pump chamber junction.

During systole, the vortex converged helically and the blood moved to pass through the apically located outlet port 22. No areas of stagnation or turbulence could be observed visually and most of the tracer disappeared during systole. A continuous spiral flow was observed through the whole cardiac cycle and is not interrupted by the onset of a new phase.

In the conventional pump, on the other hand, the ejection of tracers out of the pump during each systole was less visible due to random flow patterns and areas of recirculation. The excellent flow characteristics of the spiral-vortex pump of the invention were also clearly demonstrated by Dye Washout tests in which superior washout of the pump housing and diaphragm-body junction was proven. Washout was incomplete in the conventional pump with visible areas of stagnation.

The spiral-vortex pump of the invention was subjected to a static test. The volume of the pump was 120 ml with the diaphragm at end diastole, reducing to 45 ml at end systole, resulting in a calculated stroke volume of 75 ml. Pressure testing up to 100 psi (5700 mmHg) yielded no leakage or breakage of the pump. The diaphragm was tested for durability under full movement at a pulse rate of 120 strokes/min under zero load. No damage was observed after over three months of pumping.

Figure 15:
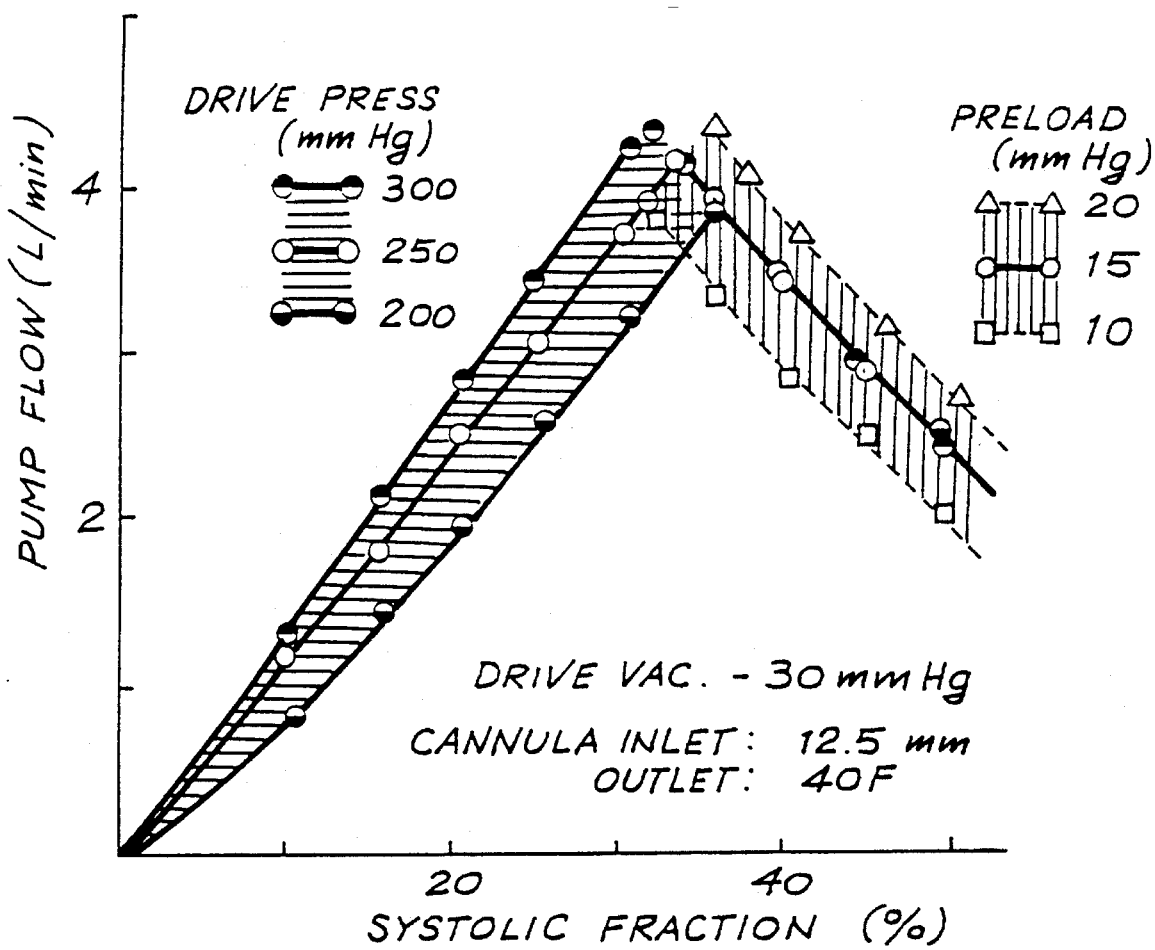
FIG. 15 is a graph of pump flow against systolic fraction for the pump shown in FIGS. 1 to 3 and, FIG. 16 is a graph of free plasma hemoglobin against pumping time for the pump shown in FIGS. 1 to 3

The spiral-vortex pump of the invention was also subjected to a dynamic test in a mock circulatory loop and performance curves obtained under various physiological driving conditions. Typical performance data is shown in FIG. 15, which shows the relationships between pump output and preload, drive pressure and systole fraction. Higher output could have been obtained if larger calibre or shorter length cannulae had been used.

Figure 16:
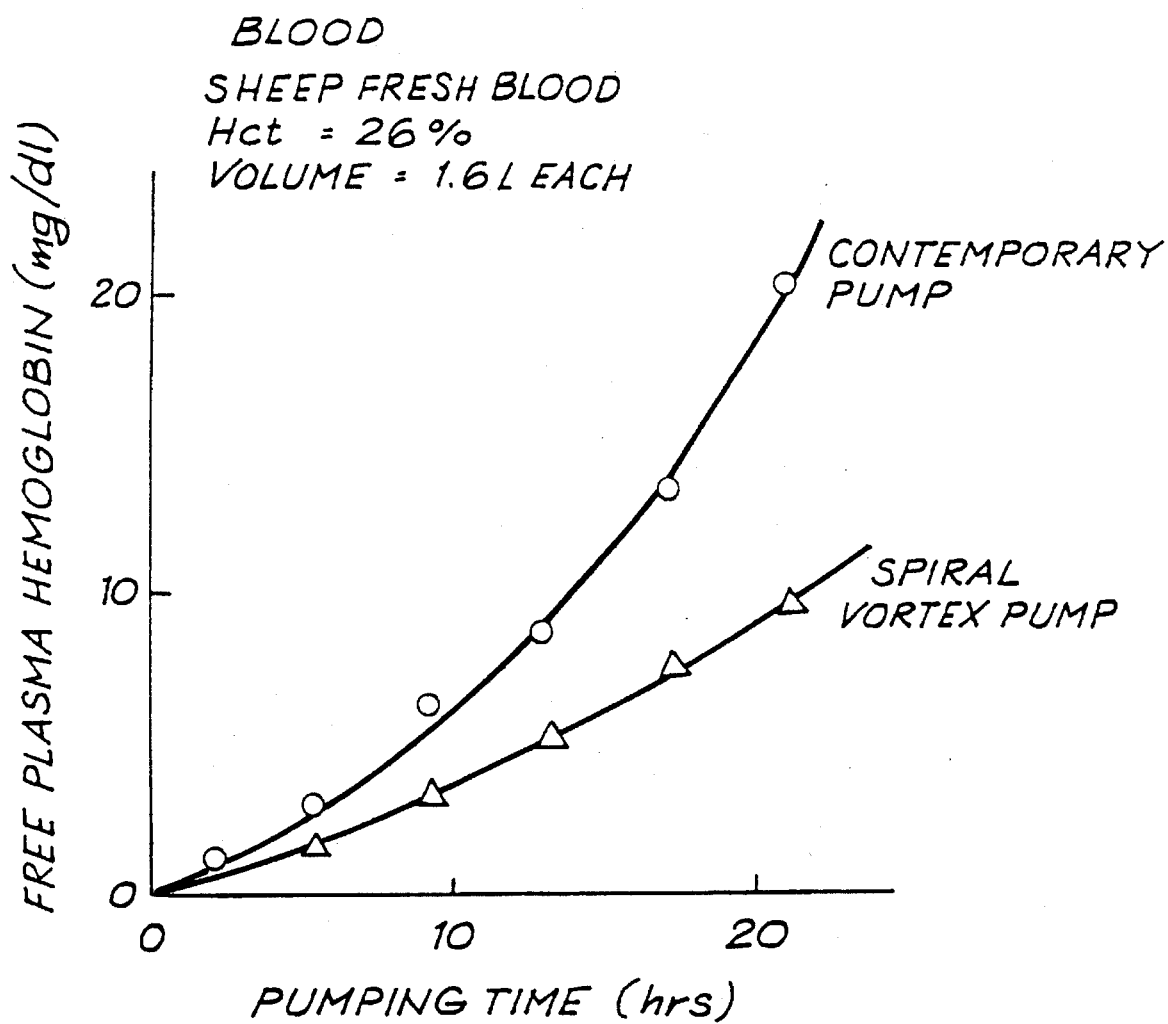

A comparative study of in vitro hemolysis between the spiral-vortex pump of the invention and a commercially available pump was carried out using 2 identical circuits, each filled with 6 litres of fresh sheep blood, with a hematocrit of 26%. With each pump operating under identical flow conditions, the blood was circulated continuously for 21 hours. Samples were taken every 4 hours for measurement of free plasma hemoglobin. The results, shown in FIG. 16, clearly show the superiority of this pump over the conventional pump in terms of hemolysis.

Although the invention has been described in relation to a conical pump chamber of specific shape and a tangential, inclined inlet of general disposition, it is to be appreciated that variations may be made and indeed may well have to be made to suit practical circumstances. The preferred angle of inclination is 45° but a range of say 20 to 30% either side of that angle should suffice. It has been established that a zero angle is inoperative as is the ninety degree angle of conventional pumps.

It is possible that the angle may change when the characteristics of the cone are modified for other uses such as pediatric use (smaller), intra aortic balloon pumping (smaller again) and arterial support (larger).

Various modifications may be made in details of design and construction without departing from the scope and ambit of the invention.

We claim:

1. A pump comprising a housing, a base, a flexible diaphragm between the housing and the base, with the diaphragm and the base defining a driving chamber and the diaphragm and the housing defining a pump chamber, an inlet to the pump chamber, an outlet from the pump chamber, a port in the driving chamber for coupling the driving chamber to a pump driver adapted to direct fluid to and from the driving chamber to drive the diaphragm, the pump chamber being of generally conical form and having a central axis with the outlet being located on and extending in the direction of the central axis at the apex of the conical pump chamber and the inlet being disposed at an angle inclined to the plane of the base of the conical pump chamber and being generally tangential to the outer portion of the base of the pump chamber such that flow through the pump chamber is in the form of a continuous spiral vortex in which (i) fluid drawn into the pump chamber by movement of the diaphragm away from the outlet enters the chamber in a downward direction that is tangential to existing flow of fluid in the chamber and flows in a circular path around the periphery of the base of the pump chamber to provide washout at the junction of the diaphragm and pump chamber with the circular cross-section of the pump chamber ensuring circular movement of the fluid, and (ii) as the diaphragm is moved towards the outlet, the fluid is constrained by fluid continuity, conservation of momentum and the conical shape of the pump chamber to form a converging helix which advances towards the apex of the conical pump chamber to be discharged through the outlet in the direction of the central axis of the pump chamber.

2. A pump according to claim 1 wherein the inlet is inclined at an angle of from 30° to 60° the plane of the base of the pump chamber.

3. A pump according to claim 1 wherein the inlet is inclined at an angle of 45° to the plane of the base of the pump chamber.

4. A pump according to claim 1 wherein the housing and the base each have peripheral flanges which are coupled together with the periphery of the diaphragm clamped and chemically bonded therebetween.

5. A pump according to claim 1 wherein the junction of the diaphragm and housing are coated with a bio-compatible material to eliminate any discontinuity at the junction.

6. A pump according to claim 4 wherein the housing and base are made from transparent epoxy and carbon fibres are embedded around the inlet and outlet, the driving chamber port and the flanges of the housing and the base.

7. A pump according to claim 1 wherein the interior surface of the inlet, outlet and pump chamber are coated with a bio-compatible material.

8. A pump according to claim 5 or claim 7 wherein the bio-compatible material is polysegmented polyurethane.

9. A pump according to claim 1 wherein the diaphragm is formed from polyvinylchloride sheet and there is a layer of bio-compatible material on each Side of the sheet.

10. A pump according to claim 1 wherein the shape of the interior of the base and that of the diaphragm are complementary.

11. A pump according to claim 10 wherein the interior surface of the base is hemi-spherical.

12. A pump according to claim 1 and further including a valve housing connected to the inlet and a valve housing connected to the outlet.

13. A pump according to claim 12 wherein the junction of the valve housing with the inlet and the junction of the valve housing with the outlet are coated with a bio-compatible material to eliminate any discontinuity at those junctions.

14. A method of pumping a fluid comprising introducing the fluid into a conical chamber closed by a diaphragm through an inlet at or adjacent the periphery of the base of the chamber at an angle inclined to the plane of the chamber base so that the fluid enters the chamber tangentially to the existing fluid flow which causes the fluid to flow in a circular path around the periphery of the chamber, operating the diaphragm in a pumping fashion so that when the diaphragm ascends the circulatory fluid is constrained by continuity and conservation of angular momentum to form a converging helix and the conical profile of the chamber results in the angular velocity of fluid increasing axially from the base plane, and, delivering the continuous spiral vortex of fluid so formed through an outlet at the apex of the conical chamber, the conical chamber having a central axis, the outlet being located on and extending in the direction of the central axis such that (i) fluid drawn into the pump chamber by movement of the diaphragm away from the outlet enters the chamber in a downward direction that is tangential to existing flow of fluid in the chamber and flows in a circular path around the periphery of the base of the pump chamber to provide washout at the junction of the diaphragm and pump chamber with the circular cross-section of the pump chamber ensuring circular movement of the fluid, and (ii) as the diaphragm is moved towards the outlet, the fluid is constrained by fluid continuity, conservation of momentum and the conical shape of the pump chamber to form a converging helix which advances towards the apex of the conical pump chamber to be discharged through the outlet in the direction of the central axis of the pump chamber.

* * * * *